(12) United States Patent
Hong et al.

(10) Patent No.: US 10,898,126 B2
(45) Date of Patent: Jan. 26, 2021

(54) TRIPLE-FUSION IMAGING DEVICE FOR SENTINEL LYMPHADENECTOMY DURING LAPAROSCOPIC SURGERY

(71) Applicants: EULJI UNIVERSITY INDUSTRY ACADEMY COOPERATION FOUNDATION, Gyeonggi-do (KR); SAMSUNG LIFE PUBLIC WELFARE FOUNDATION, Seoul (KR); KOREA INSTITUTE OF RADIOLOGICAL & MEDICAL SCIENCE, Seoul (KR)

(72) Inventors: Seong Jong Hong, Seoul (KR); Han Gyu Kang, Gyeonggi-do (KR); Gun Chul Hong, Seoul (KR); Hyung Seok Lee, Gyeonggi-do (KR); Kyeong Min Kim, Seoul (KR); Ho Young Lee, Seoul (KR); Seung Hoon Lee, Daejeon (KR); Jong Hun Lee, Seoul (KR)

(73) Assignees: EULJI UNIVERSITY INDUSTRY ACADEMY COOPERATION FOUNDATION, Gyeonggi-Do (KR); SAMSUNG LIFE PUBLIC WELFARE FOUNDATION, Seoul (KR); KOREA INSTITUTE OF RADIOLOGICAL & MEDICAL SCIENCE, Seoul (KR)

(*) Notice: Subject to any disclaimer, the term of this patent is extended or adjusted under 35 U.S.C. 154(b) by 680 days.

(21) Appl. No.: 15/563,677

(22) PCT Filed: Jan. 26, 2016

(86) PCT No.: PCT/KR2016/000792
§ 371 (c)(1),
(2) Date: Apr. 11, 2018

(87) PCT Pub. No.: WO2016/159504
PCT Pub. Date: Oct. 6, 2016

(65) Prior Publication Data
US 2018/0228424 A1    Aug. 16, 2018

(30) Foreign Application Priority Data
Apr. 2, 2015    (KR) .................. 10-2015-0046955

(51) Int. Cl.
*A61B 8/00* (2006.01)
*A61B 5/00* (2006.01)
(Continued)

(52) U.S. Cl.
CPC .......... *A61B 5/418* (2013.01); *A61B 1/00009* (2013.01); *A61B 1/042* (2013.01);
(Continued)

(58) Field of Classification Search
CPC ....... A61B 5/418; A61B 1/00009; A61B 6/00; A61B 5/004; A61B 5/0036; A61B 1/0638;
(Continued)

(56) References Cited

U.S. PATENT DOCUMENTS

| 8,473,035 B2 | 6/2013 | Frangioni | |
| 2013/0309169 A1* | 11/2013 | Kim | G01N 33/534 424/1.69 |
| 2015/0018690 A1* | 1/2015 | Kang | A61B 1/063 600/473 |

FOREIGN PATENT DOCUMENTS

| EP | 1149591 B1 | 10/2006 |
| KR | 10-1364339 | 1/2013 |

(Continued)

Primary Examiner — Joel Lamprecht
(74) Attorney, Agent, or Firm — Stuart H. Mayer; Mayer & Williams PC (57) ABSTRACT

The present invention provides a triple fusion imaging device for sentinel lymphadenectomy for laparoscopic sur-
(Continued)

gery including: a composite laparoscope for near infrared ray/gamma ray/visible ray acquisition configured to acquire triple images of a gamma ray from a gamma ray radioactive material injected to a diseased part, a visible ray, and a near infrared ray; an optical fiber configured to transmit the triple images acquired from the composite laparoscope; an optical source configured to generate a white light for acquiring a visible image through the optical fiber and a near infrared ray excitation light for acquiring a near infrared ray image by exciting a near infrared ray emitting fluorescence material at the disease part; an optical-to-electrical conversion module configured to separate individual images of the visible ray, near infrared ray and gamma ray from the triple images delivered through the optical fiber and then respectively convert the individual images to electrical signals; a matching unit configured to match a visible image signal, a near infrared image signal and a gamma ray image signal from the optical-to-electrical conversion module to one image; and an image display unit configured to display the image from the matching unit.

12 Claims, 6 Drawing Sheets

(51) Int. Cl.
*A61B 1/04* (2006.01)
*A61B 1/313* (2006.01)
*A61B 1/00* (2006.01)
*A61B 6/00* (2006.01)
*A61B 1/06* (2006.01)
*A61B 6/03* (2006.01)

(52) U.S. Cl.
CPC ............ *A61B 1/043* (2013.01); *A61B 1/0638* (2013.01); *A61B 1/3132* (2013.01); *A61B 5/004* (2013.01); *A61B 5/0036* (2018.08); *A61B 5/0084* (2013.01); *A61B 6/00* (2013.01); *A61B 6/037* (2013.01); *A61B 2505/05* (2013.01); *G06T 2210/41* (2013.01)

(58) Field of Classification Search
CPC ....... A61B 1/042; A61B 1/3132; A61B 1/043; A61B 5/0084; A61B 6/037; A61B 2505/05; G06T 2210/41
See application file for complete search history.

(56) References Cited

FOREIGN PATENT DOCUMENTS

| KR | 10-2015-0007679 | | 1/2015 |
|---|---|---|---|
| WO | 1997/03369 | A1 | 1/1997 |
| WO | 2012/021045 | A2 | 2/2012 |

* cited by examiner

TRIPLE-FUSION IMAGING DEVICE FOR SENTINEL LYMPHADENECTOMY DURING LAPAROSCOPIC SURGERY

TECHNICAL FIELD

The present invention relates to an imaging device for laparoscopic surgery, and more particularly to a triple-fusion imaging device for sentinel lymphadenectomy during a laparoscopic surgery for providing a triple-fusion image of a visible ray, a near infrared ray, and a gamma ray, which is capable of assisting sentinel lymphadenectomy during a laparoscopic surgery or a robotic surgery for tumor removal.

BACKGROUND ART

Typically, a laparoscopic surgery means a microsurgery performed using a special instrument such as a laser special surgery technique, by which the abdomen is not incised but is pieced to form a hole having 0.5 to 1 cm diameter near the navel and through which the inside of the abdomen is looked. Due to the laparoscopic surgery, a surgery risk, a stress caused by the surgery, and a period for hospitalization and recovery are dramatically reduced. A recent laparoscope with a computer chip mounted thereon may obtain a clearer and more enlarged image than that obtained through a naked eye, and thus a flow of blood may be stopped from a microvessel without any problem. In case of sparing the nerve, a nerve sparing technique is easily performed through the enlarged image.

On the other hand, a sentinel lymph node (SLN) is a lymph node from which a lymph of a primary tumor is drained at first, and whether the SLN is spread is an important index for showing whether distant metastasis is possible. Whether the SLN is spread is determined through pathologic examination after dissecting the SLN through SLN biopsy, and a proper surgery range and a final surgical plan are determined in a surgical room by means of whether the SLN is spread. Accordingly, SLN evaluation is clinically very important.

For the laparoscopic surgery, it is necessary to dissect a SLN for evaluating the SLN, but most conventional instruments show a single image and thus accurate determination is not easy. In other words, when an SLN is dissected through a robotic surgery for a prostate cancer with assistance of a near infrared camera, it is difficult to check a part of the SLN through the near infrared ray camera due to weak transmittance of near infrared fluorescence. In particular, unlike an existing surgical method, a surgery is nowadays performed with a minimum invasive surgical method, and since a percentage of the laparoscopic surgery and robotic surgery, through which one or several ports are formed in the patient's body, gradually increases, a proper SLN evaluation technique suitable for such surgical methods is necessary. Since the SLN evaluation is ultimately performed by obtaining and checking a tissue in a surgical room, a technique and equipment are necessary for evaluating the SLN while minimally influencing an existing surgery, but there is no equipment satisfying such requirements.

In addition, a blue dye and near infrared ray have been used in a typical laparoscopic surgery or robotic surgery, but there is difficulty in lymph node dissection due to weak transmission of the blue dye and near infrared ray. A gamma ray has good transmission and may compensate the weakness of the blue dye and near infrared ray. However, an instrument should be able to be inserted into the body cavities. Thus it has not been easy to develop an instrument with a small size, high sensitivity of a gamma ray, an excellent spatial resolution, and a wide visual field. It has not been either easy to develop an imaging device of high sensitivity, which is capable of providing an image within 2 to 3 minutes, since it should be available in surgery.

DISCLOSURE OF THE INVENTION

Technical Problem

The most important image provided to a surgery doctor in the laparoscopic surgery or robotic surgery is a visible ray image, but a lymph node check is not clear only with the visible ray image. Therefore, additional information will be helpful. Since a blue dye used in an SLN surgery for breast cancer has weak transmission, it is difficult to use the same for a prostate cancer. Thus a near infrared ray image is used for the prostate cancer. However, even for the near infrared ray, it is not easy to accurately check in a depth of 10 mm or deeper. In order to compensate this, a gamma probe is used. But the gamma probe only provides a count rate and does not provide an image, which results in difficulty in SLN dissection, since it does not provide a fusion image of a visible ray/near infrared ray/gamma ray.

The present invention is proposed to solve the above-described problem, and the purpose of the present invention is to provide a triple-fusion imaging device for sentinel lymphadenectomy during a laparoscopic surgery, which is capable of dissecting a sentinel lymph node with high sensitivity and specificity in laparoscopic and robotic surgeries by providing a visible ray/near infrared ray/gamma ray fusion image so that it is helpful to SLN dissection during the laparoscopic and robotic surgeries for removing a tumor.

Technical Solution

In order to achieve the above-described purpose, a triple-fusion imaging device for sentinel lymphadenectomy is characterized by including: a composite laparoscope for near infrared ray/gamma ray/visible ray acquisition configured to acquire triple images of a gamma ray from a gamma ray emitting radioactive material injected to a diseased part, a visible ray, and a near infrared ray; an optical fiber configured to transmit the triple images acquired from the composite laparoscope; an optical-to-electrical conversion module configured to separate the triple images delivered through the optical fiber into individual images of the visible ray, near infrared ray, and gamma ray, and then convert the individual images into electrical signals; a matching unit configured to match, into one image, the visible ray, near infrared ray, and gamma ray images from the optical-to-electrical conversion module; and an image display unit configured to display the image from the matching unit.

In the triple-fusion imaging device for sentinel lymphadenectomy, the composite laparoscope is configured from: an optical source configured to generate a white light for acquiring the visible ray image and an infrared excitation light for acquiring a near infrared ray image by exciting a near infrared ray emitting fluorescence material injected to a diseased part; a gamma ray scintillation crystal configured to acquire a gamma ray image from a gamma ray emitting radioactive material injected to the diseased part; a collimator configured to acquire a wide area image of the diseased part; and an optical mechanism configured to process triple images collected through the collimator to transmit the triple images to the optical fiber.

The collimator may be a pinhole collimator, and in this case, the pinhole collimator may be manufactured with tungsten. When the diameter of the pinhole is D, a unique resolution, a point source sensitivity and a sheet source sensitivity may be determined by a prescribed equation. The optical-to-electrical conversion module is configured from: a first dichroic mirror configured to separate a gamma ray scintillation in the 400 to 500 nm band from a light incident through the optical fiber; a first bandpass filter configured to pass only the gamma ray scintillation in the 400 to 500 nm band; a first CCD configured to convert the gamma ray scintillation in the 400 to 500 nm band to an electrical signal; a second dichroic mirror configured to separate a visible ray in the 500 to 700 nm band from the light passing through the first dichroic mirror; a second bandpass filter configured to pass only the visible ray in the 500 to 700 nm band; a second CCD configured to convert the visible ray in the 500 to 700 nm band to an electrical signal; a third bandpass filter configured to pass only a near infrared ray in the 790 to 875 nm band from the light passing through the second dichroic mirror; and a third CCD configured to convert the near infrared ray in the 790 to 875 nm band to an electrical signal. In addition, the optical-to-electrical conversion module may also be configured to make the light incident through the optical fiber pass a filter rotator and then be received by one CCD. The filter rotator is configured from: the first bandpass filter configured to pass only the gamma ray scintillation light in the 400 to 500 nm band; the second bandpass filter configured to pass only the visible ray of 500 to 700 nm band; and the third bandpass filter configured to pass only the infrared ray in the 790 to 875 nm band. The matching unit may be implemented with a computer (PC) configured to remove a noise so that each CCC image input from the optical-to-electrical conversion module has the same visual field.

Advantageous Effects

The triple-fusion imaging device for sentinel lymph-adenectomy for laparoscopic surgery may provide a visible ray/near infrared ray/gamma ray fusion image within a short time, e.g. 2 to 3 minutes, to enable a sentinel lymph node to be dissected with high sensitivity and specificity in laparo-scopic and robotic surgeries. Therefore a side effect occurring by removing an unnecessarily wide lymph node may be reduced and significantly improve quality of life of an old aged senior. Furthermore, according to the present invention, since fusion of the visible ray, near infrared ray, and gamma ray images may be accurately and rapidly processed to provide the fusion image within 2 to 3 minutes by making visual fields of a visible ray, a near infrared ray, and a gamma ray equal, it is advantageous that a surgery doctor may remove the sentinel lymph node while watching the fusion image.

MODE FOR CARRYING OUT THE INVENTION

According to an aspect of the present invention, a triple fusion imaging device for sentinel lymphadenectomy for laparoscopic surgery is provided which includes: a composite laparoscope for near infrared rat/gamma ray/visible ray acquisition configured to acquire triple images of a gamma ray from a gamma ray radioactive material injected to a diseased part, a visible ray, and a near infrared ray; an optical fiber configured to transmit the triple images acquired from the composite laparoscope; an optical source configured to generate a white light for acquiring a visible image through the optical fiber and a near infrared ray excitation light for acquiring a near infrared ray image by exciting a near infrared ray emitting fluorescence material at the disease part; an optical-to-electrical conversion module configured to separate individual images of the visible ray, near infrared ray and gamma ray from the triple images delivered through the optical fiber and then respectively convert the individual images to electrical signals; a matching unit configured to match a visible image signal, a near infrared image signal and a gamma ray image signal from the optical-to-electrical conversion module to one image; and an image display unit configured to display the image from the matching unit.

In the triple fusion imaging device for sentinel lymphadenectomy for laparoscopic surgery, the composite laparoscope for near infrared rat/gamma ray/visible ray acquisition may be configured from: a lens configured to concentrate the visible ray and the near infrared ray to a focus; a collimator configured to remove an unnecessary background gamma ray for gamma ray imaging or counting scheme, and for acquiring a wide area image; a gamma ray scintillation crystal configured to obtain a gamma ray scintillation image by reacting with a gamma ray emitted from a radioactive material injected to the diseased part; and an optical mechanism by which sensitivities and resolutions of the near infrared ray and gamma ray are adjustable by changing distances between the components.

In the triple fusion imaging device for sentinel lymphadenectomy for laparoscopic surgery, the collimator may be a diverging collimator, a parallel multi-hole collimator, or a single or multi-hole pinhole collimator.

In the triple fusion imaging device for sentinel lymphadenectomy for laparoscopic surgery, when the collimator is a pinhole collimator and a diameter of the pinhole is D, a unique resolution of the gamma ray, point source sensitivities and sheet source sensitivities of the gamma ray, the near infrared ray and the visible ray may be determined by prescribed equations. In addition, in the pinhole collimator, a tungsten collimator is replaceable by another by using a rotary wheel, and 5 to 7 tungsten blades of which are assembled to freely adjust a diameter of a hole from 0.5 mm to 8 mm.

In the triple fusion imaging device for sentinel lymphadenectomy for laparoscopic surgery, the near infrared ray emitting fluorescence material may be indocyanine green.

In the triple fusion imaging device for sentinel lymphadenectomy for laparoscopic surgery, the gamma ray radioactive material may be a compound containing $^{99m}$Tc, for example, the compound containing $^{99m}$Tc may be $^{99m}$Tc-antimony sulfide, $^{99m}$Tc-sulfur colloid, $^{99m}$Tc-nano-colloid, $^{99m}$Tc-human serum albumin, and $^{99m}$Tc-phytate colloid.

In the triple fusion imaging device for sentinel lymphadenectomy for laparoscopic surgery, the gamma ray scintillation crystal may be GSO, BGO, or CsI(Tl).

In the triple fusion imaging device for sentinel lymphadenectomy for laparoscopic surgery, the optical-to electrical conversion module may be configured from: a first dichroic mirror configured to separate a gamma ray scintillation in a 400 to 500 nm band from a light incident through the optical fiber; a first bandpass filter configured to pass only the gamma ray scintillation in the 400 to 500 nm band; a first CCD configured to convert the gamma ray scintillation in the 400 to 500 nm band to an electrical signal; a second dichroic mirror configured to separate a visible ray in a 500 to 700 nm band from a light passing through the first dichroic mirror; a second bandpass filter configured to pass only the visible ray in the 500 to 700 nm band; a second CCD configured to convert the visible ray in the 500 to 700 nm band to an electrical signal; and a third bandpass filter configured to pass only a near infrared ray in a 790 to 875 nm band from a light passing through the second dichroic mirror; and a third CCD configured to convert the near infrared ray in the 790 to 875 nm band to an electrical signal.

In the triple fusion imaging device for sentinel lymphadenectomy for laparoscopic surgery, the optical-to-electrical conversion module may be configured from: one CCD; and a filter rotator configured from: a first bandpass filter configured to pass only a gamma ray scintillation in a 400 to 500 nm band; a second bandpass filter configured to only pass a visible ray in a 500 to 700 nm band; and a third bandpass filter configured to pass only an infrared ray in a 790 to 875 nm band.

In the triple fusion imaging device for sentinel lymphadenectomy for laparoscopic surgery, the matching unit, by being implemented with a computer (PC) configured to remove a noise so as to make each CCD image input from the optical-to-electrical conversion module have the same visual field, may remove a noise for each frame of a gamma ray signal image incident to a first CCD with a median filter, and a total brightness value and a number of pixels having a value equal to or greater than a threshold value calculated in advance may be calculated to be available as a real time counting mode.

The triple fusion imaging device for sentinel lymphadenectomy for laparoscopic surgery may further include a fiber optic taper configured to deliver the visible ray image, infrared ray image, and the gamma ray image to the optical fiber.

Hereinafter, exemplary embodiments of the present invention will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Also, sizes of elements in the drawings may be exaggerated for convenience of explanation.

Figure 1:
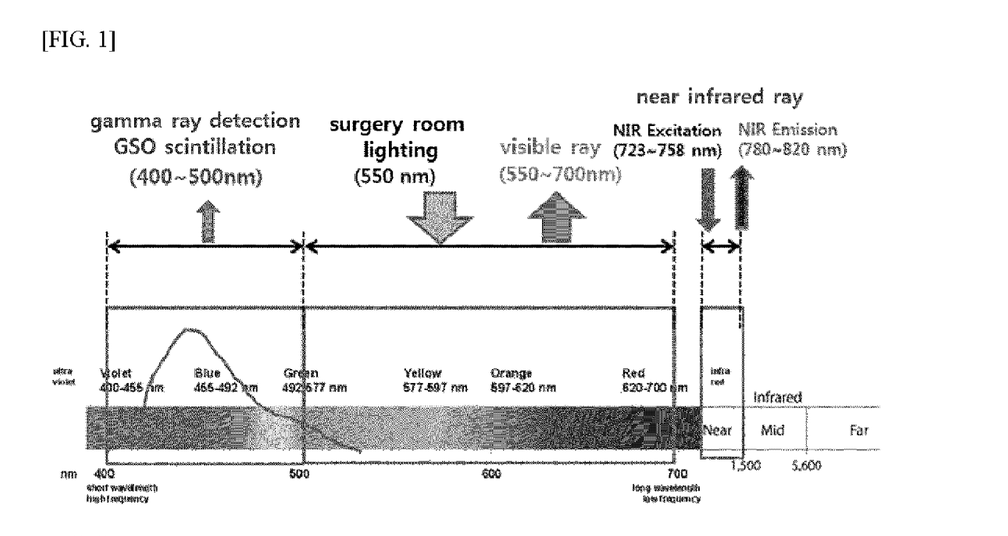
FIG. 1 is a drawing illustrating wavelength distributions of a gamma ray, a visible ray, and a near infrared ray used in the present invention.

FIG. 1 is a drawing illustrating wavelength distributions of a gamma ray, a visible ray, and a near infrared ray used in the present invention. A triple fusion imaging device for sentinel lymphadenectomy according to an embodiment of the present invention is, as shown in FIG. 1, a device capable of showing, to a doctor in surgery, a surgery image obtained by acquiring a gamma ray image by GSO scintillation light in the 400 to 500 nm band, a visible ray image in the 550 to 700 nm band and a near infrared ray (NIR) image in the 790 to 830 nm band with a near infrared excitation light in the 730 to 760 nm band, and matching the obtained images into one image via signal processing.

Figure 2:
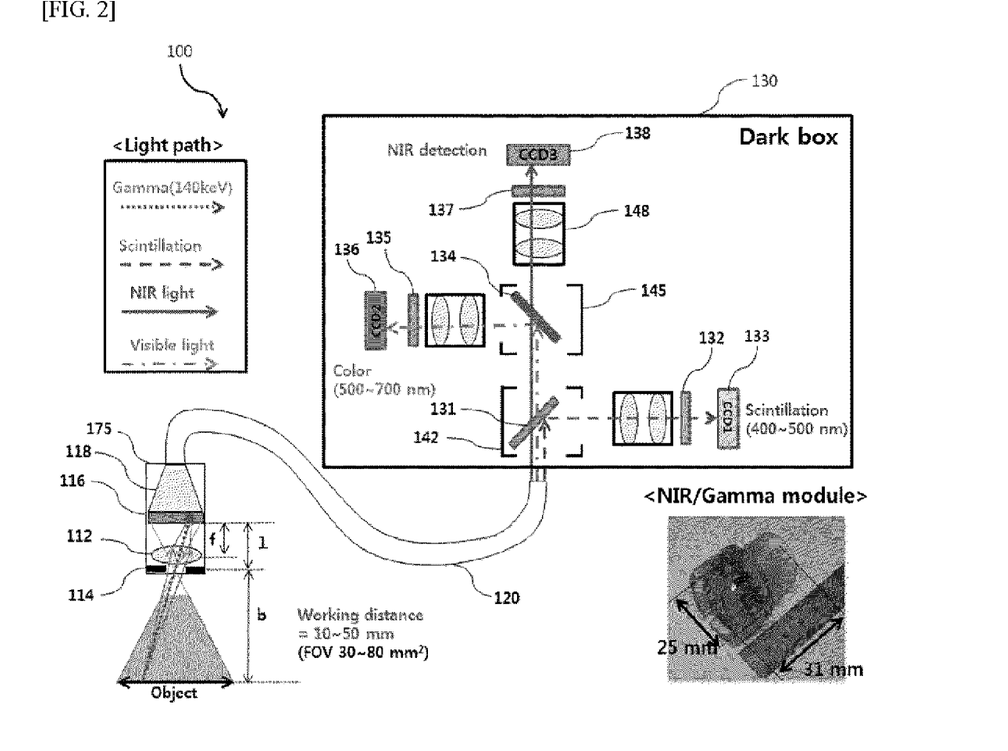
FIG. 2 is a conceptual diagram schematically illustrating a structure of a triple fusion imaging device according to an embodiment of the present invention.

FIG. 2 is a conceptual diagram schematically illustrating a structure of a triple fusion imaging device according to an embodiment of the present invention, and is an example (first embodiment) of concurrent detection. First, in order to use the triple fusion imaging device 100 for sentinel lymphadenectomy according to the first embodiment of the present invention, it is necessary to inject $^{99m}$Tc+ICG material for emitting a gamma ray and an NIR to a diseased part.

Thereafter, the first embodiment 100 of the triple fusion imaging device according to the present invention, which provides triple images for a sentinel lymph node surgery for a diseased part, is configured from, as shown in FIG. 2: a composite laparoscope for near infrared ray/gamma ray/visible ray image acquisition 110 configured to acquire triple images of a visible ray, a near infrared, and a gamma ray; an optical fiber 120 configured to transmit the triple images received from the composite laparoscope; an optical-to-electrical conversion module 130 configured to separate the triple images delivered through the optical fiber 120 into individual images of the visible ray, the near infrared, and the gamma ray, and convert the individual images to electrical signals; and a PC 140 configured to match, to one image, the visible image signal, the near infrared image signal, and the gamma image signal from the optical-to-electrical conversion module 130, and display the one image.

Referring to FIG. 2, the composite laparoscope for near infrared ray/gamma ray/visible ray image acquisition 110 is configured from: an optical source 111 configured to generate a white light for acquiring the visible image through the optical fiber and a near infrared excitation light for generating a near infrared ray excitation light for exciting a near infrared ray emitting material (ICG; Indocyanine green) at the diseased part to acquire the near infrared ray image; a lens 112 configured to concentrate to focus the visible ray and near infrared ray signals; a tungsten pinhole collimator 114 configured to remove an unnecessary background gamma ray for gamma ray imaging or counting scheme and acquire a wide area image; a gamma ray scintillation crystal 116 configured to obtain a gamma ray image via the pinhole collimator from the gamma ray emitting material, e.g. $^{99m}$Tc, injected to the diseased part; and a fiber optic taper 118 configured to deliver the visible ray image, the near infrared image, and the gamma ray image to the optical fiber 120. The fiber optic taper plays a role of widening a visual field and may be omitted for enhancing an image delivery efficiency. In addition, although not shown in the drawing, the composite laparoscope for near infrared ray/gamma ray/visible ray image acquisition 110 is provided with an optical mechanism capable of adjusting sensitivities and resolutions of the near infrared ray and gamma ray by changing distances between components. Without the pinhole collimator 114, it is not possible to find a location of a tumor, since all tumors or background gamma rays enter the entire area of the gamma ray scintillation crystal 116 and react. But in the present invention, when a pinhole collimator having the diameter of several mm is used, a reaction area in which the gamma ray may react with the gamma ray scintillation crystal 116 is determined to be small. Therefore tumor imaging is enabled. Although the pinhole collimator 114 is exemplified in the embodiment of the present invention, a diverging collimator, a parallel multi-hole collimator, or a pinhole collimator may be used, and the collimator may be manufactured with tungsten. Furthermore, since requirements of a scintillation crystal available in detection of a gamma ray of 20 to 250 keV are not to have deliquescence, not to include own natural radioactivity, but to have a scintillation amount as much as possible, Gadolinium oxyorthosilicate (GSO, $Gd_2SiO_5$) is proper. Bismuth germanate (BGO, $Bi_4Ge_3O_{12}$) has an advantage of making thickness thin due to a high density, but a scintillation amount is small. For concurrent images of gamma ray/near infrared ray/visible ray, Cesium Iodide crystals doped with Cesium Iodide crystals doped with Thallium (CsI(Tl)) has an advantage of less light spread and is advantageous in a light emission amount, since a scintillation crystal may be grown in a pillar shape despite of a lower density than that of GSO. But it has disadvantages that it shows little deliquescence and a maximum light emitting wavelength area of which largely overlaps a xenon lamp wavelength in a visible ray area.

Gamma ray measurement is performed by locating a gamma ray scintillation crystal before the optical fiber and measuring scintillation light generated from the gamma ray scintillation crystal reacting with a gamma ray. For example, a scintillation crystal having 1 to 2 mm thickness is attached to a front end of a bunch of optical fibers of 4×4 $mm^2$ configured from optical fibers having the diameter of 10 μm. In addition, a design of the collimator is important, since the gamma ray sensitivity and location resolution of an imaging device are determined by such as the diameter of an optical fiber, the thickness and hole size of a collimator, and the depth of a ray source.

Figure 5:
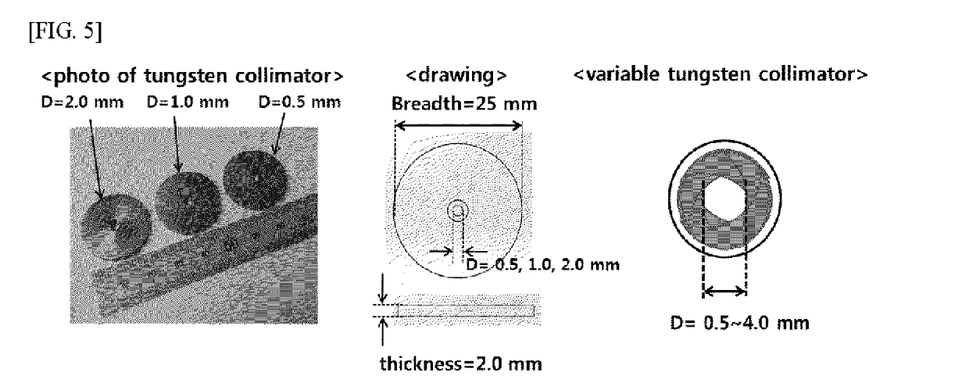
FIG. 5 is a conceptual diagram illustrating various structures of a pinhole collimator according to the embodiments of the present invention illustrated in FIGS. 2 to 4.

As shown in FIG. 5, the pinhole collimator 114 according to the present invention is an example that a pinhole is manufactured to have the diameter of 2 mm, 1 mm, and 0.5 mm, and the pinhole collimator 114 may be manufactured with tungsten. Referring to FIG. 5, a tungsten collimator may be replaced by another by using a rotary wheel, and 5 or 7 tungsten blades of which may be assembled so that the hole diameter is freely adjustable from 0.5 mm to 8 mm. When the unique resolution of the scintillation crystal is assumed to be 0.5/1.0/2.5 mm, the spatial resolution, the point source sensitivity and the sheet source sensitivity are as the following Tables 1 to 3.

TABLE 1

| Spatial resolution | Hole diameter (mm) | | | | |
|---|---|---|---|---|---|
| | 1.0 | 1.5 | 2.0 | 2.5 | 3.0 |
| hole to object distance (mm) | | | | | |
| 10 | 2.1/2.3/3.2 | 3.1/3.2/4.0 | 4.1/4.2/4.8 | 5.1/5.2/5.6 | 6.1/6.1/6.6 |
| 20 | 3.2/3.7/5.9 | 4.7/5.0/6.8 | 6.2/6.4/7.9 | 7.7/7.9/9.1 | 9.2/9.3/10.4 |
| 30 | 4.4/5.1/8.6 | 6.3/6.8/9.7 | 8.3/8.7/11.1 | 10.2/10.6/12.6 | 12.2/12.5/14.3 |
| 40 | 5.5/6.5/11.3 | 7.9/8.6/12.6 | 10.4/10.9/14.3 | 12.8/13.3/16.1 | 15.3/15.7/18.2 |
| 50 | 6.7/8.0/14.0 | 9.5/10.5/15.5 | 12.4/13.2/17.5 | 15.4/16.0/19.7 | 18.4/18.9/22.1 |

TABLE 2

| Spatial resolution | Hole diameter (mm) | | | | |
|---|---|---|---|---|---|
| | 1.0 | 1.5 | 2.0 | 2.5 | 3.0 |
| hole to object distance (mm) | | | | | |
| 10 | $6.3 \times 10^{-4}$ | $1.4 \times 10^{-3}$ | $2.5 \times 10^{-3}$ | $6.3 \times 10^{-4}$ | $6.3 \times 10^{-4}$ |
| 20 | $1.6 \times 10^{-4}$ | $3.6 \times 10^{-4}$ | $6.4 \times 10^{-4}$ | $6.3 \times 10^{-4}$ | $6.3 \times 10^{-4}$ |
| 30 | $6.9 \times 10^{-5}$ | $1.5 \times 10^{-4}$ | $2.8 \times 10^{-4}$ | $6.3 \times 10^{-4}$ | $6.3 \times 10^{-4}$ |
| 40 | $3.9 \times 10^{-5}$ | $8.8 \times 10^{-5}$ | $6.3 \times 10^{-4}$ | $6.3 \times 10^{-4}$ | $6.3 \times 10^{-4}$ |
| 50 | $2.5 \times 10^{-5}$ | $5.6 \times 10^{-5}$ | $6.3 \times 10^{-4}$ | $6.3 \times 10^{-4}$ | $6.3 \times 10^{-4}$ |

TABLE 3

| Spatial resolution | Hole diameter (mm) | | | | |
|---|---|---|---|---|---|
| | 1.0 | 1.5 | 2.0 | 2.5 | 3.0 |
| hole to object distance to (mm) 10 | 0.11/3.5 × 10⁻⁴ | 0.25/1.1 × 10⁻⁴ | 0.44/1.4 × 10⁻³ | 0.69/2.2 × 10⁻³ | 0.99/3.2 × 10⁻³ |
| 20 | 0.11/8.8 × 10⁻⁵ | 0.25/2.0 × 10⁻⁴ | 0.44/3.5 × 10⁻⁴ | 0.69/5.5 × 10⁻⁴ | 0.99/7.9 × 10⁻⁴ |
| 30 | 0.11/3.9 × 10⁻⁵ | 0.25/5.1 × 10⁻⁵ | 0.44/1.6 × 10⁻⁴ | 0.69/2.4 × 10⁻⁴ | 0.99/3.5 × 10⁻⁴ |
| 40 | 0.11/2.2 × 10⁻⁵ | 0.25/5.1 × 10⁻⁵ | 0.44/8.8 × 10⁻⁵ | 0.69/1.4 × 10⁻⁴ | 0.99/2.0 × 10⁻⁴ |
| 50 | 0.11/1.4 × 10⁻⁵ | 0.25 × 3.2/10⁻⁵ | 0.44/5.6 × 10⁻⁵ | 0.69/8.8 × 10⁻⁵ | 0.99/1.3 × 10⁻⁴ |

When the pinhole size is small, it may be known that a system resolution greatly depends on the unique resolution. The sensitivity for the sheet source is a sensitivity when point sources are uniformly distributed across the visual field with a ratio of 1 Bq per unit area, and 0.44 gamma rays per second reacts with the scintillation crystal, regardless of a distance between an imaging target and the pinhole. It may be also known that as the distance between the imaging target and the pinhole is greater, the spatial resolution is lowered and the sensitivity is also very low.

Figure 6:
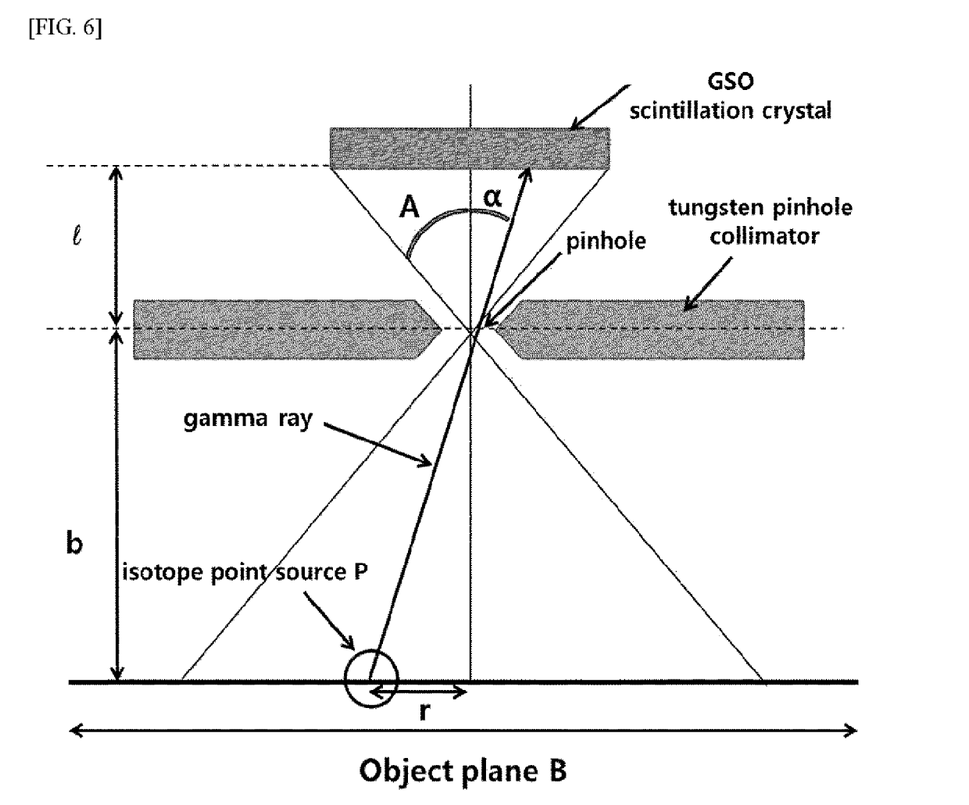
FIG. 6 is a conceptual diagram illustrating a principle of the pinhole collimator according to the embodiments of the present invention illustrated in FIGS. 2 to 4.
Figure 7:
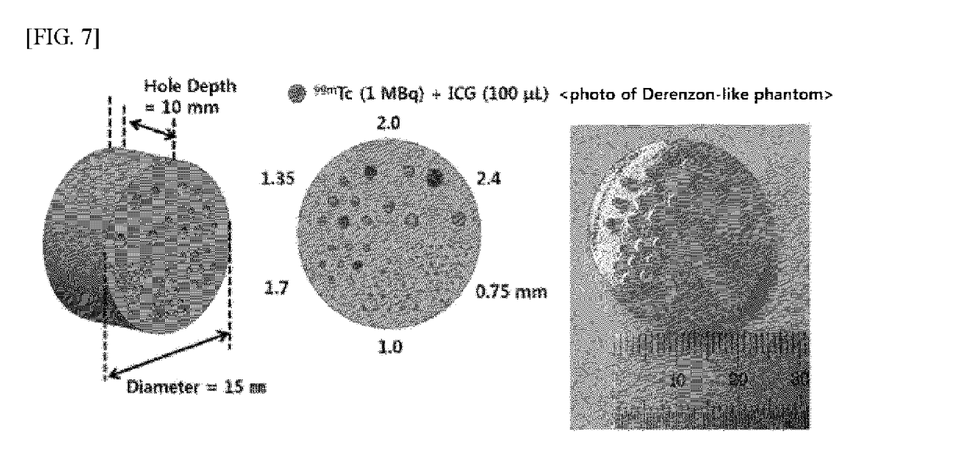
FIG. 7 illustrates a structure of a phantom for sequentially acquiring gamma ray/near infrared ray images and an actually manufactured phantom in an embodiment of the present invention.

Referring to FIG. 6, when the diameter of the pinhole collimator 114 is d, the spatial resolution, the point source sensitivity and the sheet source sensitivity of the pinhole collimator 114 may be respectively obtained using the following equations.

<Spatial Resolution where d Denotes the Diameter of a Pinhole, and Ri Denotes Unique Resolution>

$$R_0 = \sqrt{\left(\frac{l+b}{l} \cdot d_0\right)^2 + \left(\frac{b}{l} \cdot R_i\right)^2}$$

$$d_0 = \sqrt{d \cdot (d + 2 \cdot \mu^{-1} \cdot \tan(A))}$$

<Point Source Sensitivity>

$$g = \begin{cases} \frac{d_0^2}{16 \cdot b^2} \cdot \cos^3(\alpha) & \text{for } \alpha < A \\ 0 & \text{for } \alpha < A \end{cases}$$

<Sheet Source Sensitivity>

$$G = \left[-\frac{d_0^2 \cdot \pi}{8} \cdot \cos(\alpha)\right]_0^A$$

In addition, the optical-to-electrical module 130 of the first embodiment, as shown in FIG. 2, is configured from: a gamma ray image processing unit formed of a first dichroic mirror 131, a first bandpass filter 132, and a first CCD 133; a visible ray image processing unit formed of a second dichroic mirror 134, a second bandpass filter 135, and a second CCD 136; and an NIR image processing unit formed of a third bandpass filter 136 and a third CCD 138.

The first dichroic mirror 131 separates a gamma ray scintillation in the 400 to 500 nm band from a light incident through the optical fiber 120, the first bandpass filter 132 only passes the gamma ray scintillation in the 400 to 500 nm band and removes a noise, and the first CCD 133 converts the gamma ray scintillation in the 400 to 500 nm band to an electrical signal. At this point, instead of the first CCD 133 for detecting the scintillation, a photomultiplier (PMT) or a silicon PMT (SiPM) may be used, and when the first CCD 133 is used, an image-intensifier tube such as a micro channel plate (MCP) may be located on a front side of the first CCD 133 to amplify the scintillation signal.

The second dichroic mirror 134 separates a visible ray in the 500 to 700 nm from light having passed the first dichroic mirror 131, the second ban pass filter 135 only passes the visible ray in the 500 to 700 nm and removes a noise, and the second CCD 136 converts the visible ray in the 500 to 700 nm to an electrical signal. The first dichroic mirror 134 separates a gamma ray scintillation in the 500 to −700 nm band from a light incident through the optical fiber 131, the first bandpass filter 135 only passes the gamma ray scintillation in the 500 to 700 nm band and removes a noise, and the first CCD 136 converts the gamma ray scintillation in the 500 to 700 nm band to an electrical signal.

The third bandpass filter 137 passes only an NIR in the 790 to 875 nm band and removes a noise, and the third CCD 138 converts the NIR in the 790 to 875 nm band to an electrical signal.

The PC 140 matches individual CCD camera images input through a USB from the optical-to-electrical conversion module 130 in order to have the same visual field.

Figure 3:
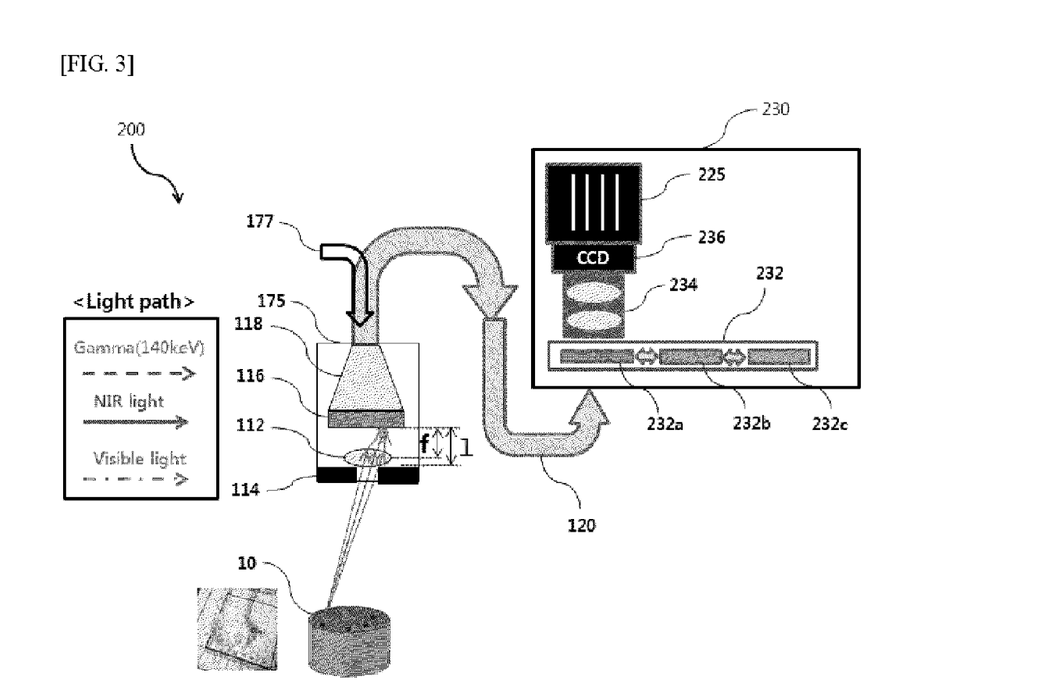
FIG. 3 is a conceptual diagram schematically illustrating a structure of a triple fusion imaging device according to another embodiment of the present invention.
Figure 4:
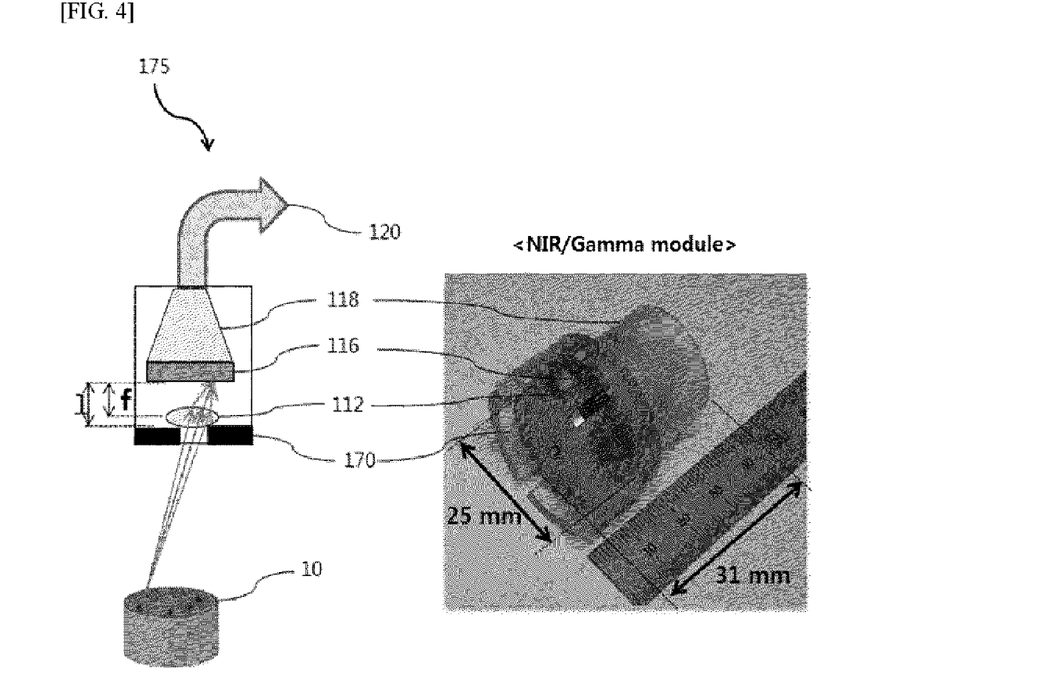
FIG. 4 is a conceptual diagram schematically illustrating a structure of a composite laparoscope for visible ray/near infrared ray/gamma ray acquisition illustrated in FIGS. 2 and 3.

FIG. 3 is, as a conceptual schematically illustrating a structure of a triple fusion imaging device according to another embodiment of the present invention, is an example (second embodiment) of a sequential detection.

First, in order to use the triple fusion imaging device 200 for sentinel lymphadenectomy for laparoscopic surgery according to the second embodiment of the present invention, as a gamma ray emitting material for emitting a gamma ray to a diseased part, it is necessary to inject a compound including a gamma ray emitting radioisotope, e.g. $^{99m}$Tc, and an NIR emitting fluorescence material, e.g. indocyanine green.

As shown in FIG. 3, the second embodiment 200 of the triple fusion imaging device according to the present invention for providing triple images for a sentinel lymph node surgery from a diseased part is configured from: a composite laparoscope for NIR/gamma ray/visible ray image acquisition 210 configured to acquire the triple images of the visible ray, the NIR, and the gamma ray; an optical fiber 220 configured to transmit the triple images acquired from the composite laparoscope 210; an optical-to-electrical conversion module 230 configured to separate individual images of the visible ray, the NIR, and the gamma ray from the triple images delivered through the optical fiber 220; and a PC 240 configured to match a visible ray image signal, an NIR image signal, and a gamma ray image signal into one image and display the one image.

Referring to FIG. 3, the composite laparoscope for NIR/gamma ray/visible ray image acquisition 210 is configured from: an optical source 211 configured to generate a white light for acquiring the visible ray image through the optical fiber and an NIR excitation light for acquiring the NIS image by exciting an NIR emitting material [e.g. indocyanine green (ICG)] at the diseased part; a lens 212 configured to concentrate signals of the visible ray and the near infrared ray to a focus; a tungsten pinhole collimator 214 configured to remove an unnecessary background gamma ray for gamma ray imaging or counting scheme and acquire a wide area image; a gamma ray scintillation crystal 216 configured to obtain a gamma ray image via the pinhole collimator from the gamma ray emitting radioisotope, e.g. $^{99m}$Tc, injected to the diseased part; and a fiber optic taper 218 configured to deliver the visible ray image, the near infrared image, and the gamma ray image to the optical fiber 220. The gamma/NIR/visible ray module 210 of the second embodiment has the same configuration as the first embodiment, and thus a further description thereabout will be omitted, and the optical-to-electrical conversion module 230 of the second embodiment, which has a different configuration from the first embodiment, will be mainly described.

The optical-to-electrical conversion module 230 of the second embodiment, as shown in FIG. 3, is configured to make a light incident through the optical fiber 220 pass a filter rotator 232 and then be received by one CCD 236. The filter rotator 232 is configured from: a first bandpass filter 232a configured to pass only a gamma ray scintillation in the 400 to 500 nm band; a second bandpass filter configured to pass only a visible ray in the 500 to 700 nm band; and a third bandpass filter 232c configured to pass only an NIR in the 790 to 875 nm band. In addition, one to one relay lens 234 may be located between the CCD 236 and the filter rotator 232.

Figure 8:
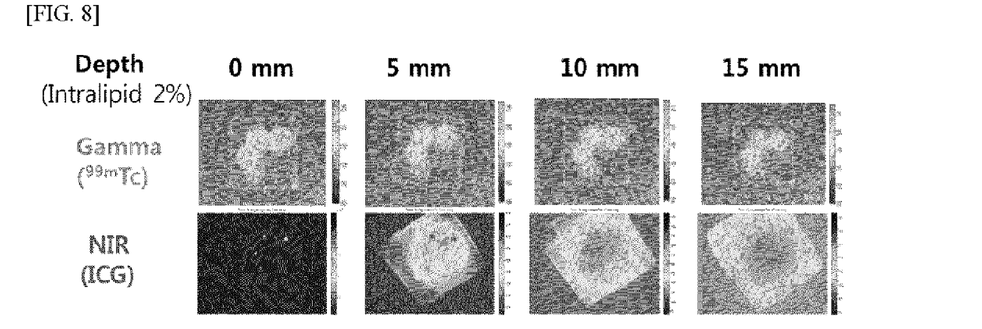
FIG. 8 is a series of photographs showing a result of sequential gamma ray/near infrared light images acquired by using a hybrid contrast agent filled phantom, which is illustrated in FIG. 7 and to which a gamma ray radioactive material and ICG fluorescence material are loaded, with a triple fusion imaging device according to an embodiment of the present invention.
Figure 9:
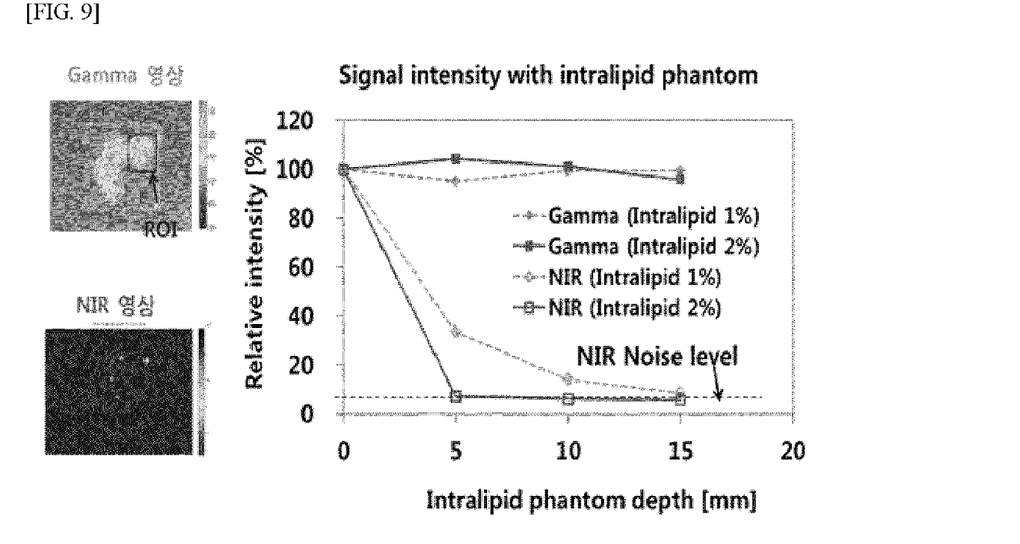
FIG. 9 shows sequential gamma ray/near infrared light images (left) acquired by using a hybrid contrast agent filled phantom, which is illustrated in FIG. 7 and to which a gamma ray radioactive material and ICG fluorescence material are loaded, with a triple fusion imaging device according to an embodiment of the present invention, and a graph (right) showing relative strengths of the gamma ray and near infrared light images.
Figure 10:
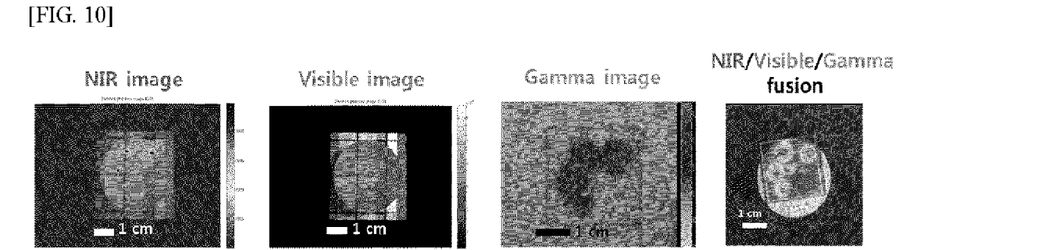
FIG. 10 shows sequential gamma ray/near infrared light images acquired by using a hybrid contrast agent filled phantom, which is illustrated in FIG. 7 and to which a gamma ray emitting radioactive material and ICG fluorescence material are loaded, with a triple fusion imaging device according to an embodiment of the present invention, and an image that those images are superimposed (in order from left)

Referring to FIGS. 8 to 10, as a verification result through an IVIS spectrum optical imaging device, it can be checked that the triple fusion imaging device according to the present invention normally operates in sequential images of the visible ray, gamma ray and NIR.

In a preferred embodiment of the present invention, the ICG is used as the NIR emitting fluorescence material, and a radioisotope for emitting a gamma ray is used as a gamma ray emitting radioisotope material, for example, a compound to which $^{99m}$Tc emitting a 140 keV gamma ray is introduced. The compound containing $^{99m}$Tc may be $^{99m}$Tc-antimony sulfide, $^{99m}$Tc-sulfur colloid, $^{99m}$Tc-nanocolloid, $^{99m}$Tc-human serum albumin, or $^{99m}$Tc-phytate colloid.

However, since ICG is a unique NIR emitting fluorescence material approved by the FDA at this time, it is preferable to use ICG, but a skilled person in the art may sufficiently understand that any NIR emitting fluorescence material currently developed or to be developed may also be adopted. Furthermore, in the same manner for the radioisotope, a gamma ray emitting radioisotope such as $^{125}$I or $^{103}$Pd may also be used in addition to $^{99m}$Tc. For visible ray detection, a xenon lamp is illuminated into the abdominal cavity to obtain a visual image of a surgery part, and for NIR detection, a filter is mounted on optical path of the xenon lamp, an NIP of near ~750 nm is irradiated to ICG injected to a human body, and an emitted NIR of near ~850 nm is detected by a CCD.

A gamma ray of 140 keV emitted from $^{99m}$Tc reacts with a scintillation crystal to generate scintillations, and each location of which is detected using the pinhole collimator and a first CCD. In other words, in the present invention, each of several hundreds to several thousand scintillations emitted by one gamma ray is used for an image configuration, and thus a statistical error is reduced and a gamma ray image is provided within a short time of about 10 seconds. In order to acquire an image of a wide visual field, a pinhole collimator is used.

Figure 11:
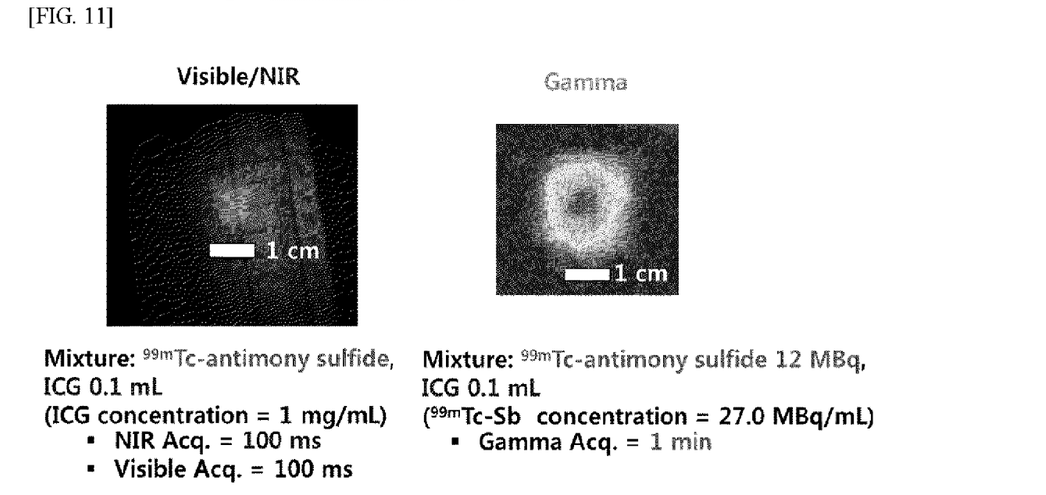
FIG. 11 is a series of photographs showing sequential images of near infrared image (left) and gamma ray scintillation image (right) obtained by imaging, with a triple fusion imaging device according to an embodiment of the present invention, a cuvette in which a mixture of a gamma ray emission radioactive material ($^{99m}$Tc—Sb colloid) and a near infrared ray fluorescence material (ICG) is contained for mapping a sentinel lymph node of a mouse.

FIG. 11 is a series of photographs showing sequential images of NIR image (left) and gamma ray scintillation image (right) obtained by imaging, with a triple fusion imaging device according to an embodiment of the present invention, a cuvette in which a mixture of a gamma ray emission radioactive material ($^{99m}$Tc—Sb colloid) and a NIR fluorescence material (ICG) is contained for mapping a sentinel lymph node of a mouse. For the mapping of the sentinel lymph node of the mouse, inventors of the present invention mixed 0.1 ml ICG solution of 1 mg/ml and 0.444 ml $^{99m}$Tc-antimony sulfide colloid of 27.0 MBq/ml, injected 0.544 ml mixture of 12 MBq $^{99m}$Tc-antimony sulfide+0.1 mg ICG to the mouse, and then acquired visual ray, NIR, and gamma ray images with the triple fusion imaging device according to an embodiment of the present invention. Specifically, the inventors applied an exposure time of 100 ms to the visual ray and NIR and checked that a pseudo-green ICG fluorescent image was shown to be superimposed on an upper portion of the visible ray (see the left column of FIG. 11). Meanwhile, for the gamma ray, an exposure of 1 min was applied and an image shown in the right column of FIG. 11 was checked.

Figure 12:
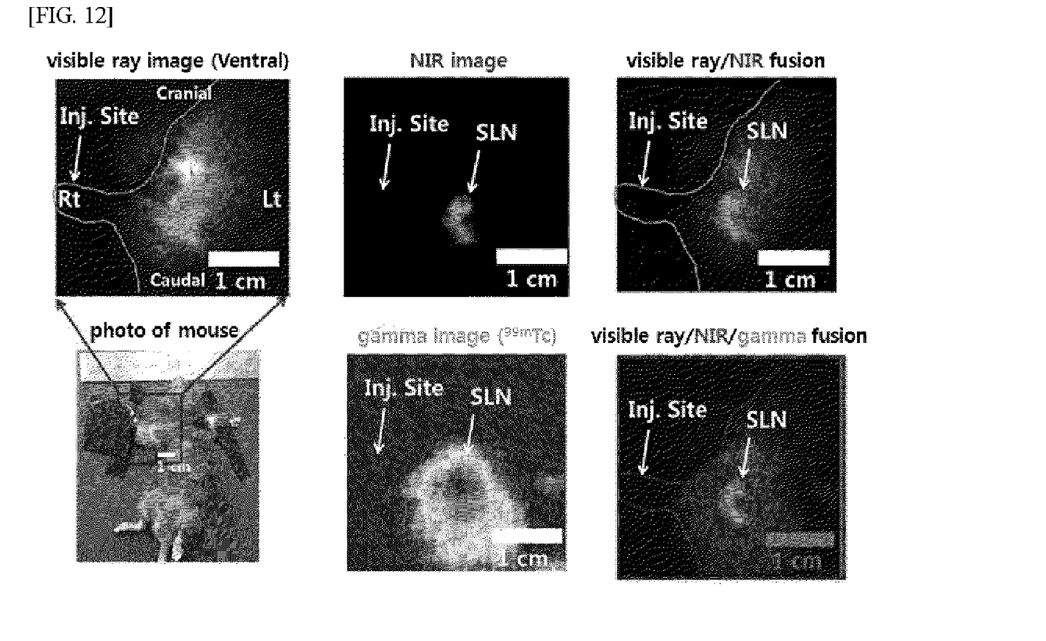
FIG. 12 shows sequential images and a superimposition image of visible ray/near infrared light/gamma ray images obtained by imaging, with a triple fusion imaging device according to an embodiment of the present invention, a sentinel lymph node of the mouse to which a mixture of a gamma ray emission radioactive material ($^{99m}$Tc—Sb colloid) and a near infrared ray fluorescence material (ICG) is injected.

FIG. 12 shows sequential images and a superimposition image of visible ray/NIR/gamma ray images obtained by imaging, with a triple fusion imaging device according to an embodiment of the present invention, a sentinel lymph node of the mouse to which a mixture of a gamma ray emission radioactive material ($^{99m}$Tc-antimony sulfide colloid) and an NIR fluorescence material (ICG) is injected. As shown, images were acquired after $^{99m}$Tc+ICG was injected to a diseased part, and a visual ray image appeared black and white by use of a black and white CCD camera, and NIR and gamma ray images appeared virtual colors representing the signal strengths. In particular, the NIR was checked to have an excellent resolution. Furthermore, as a result of fusing the visual ray, the NIR, and the gamma ray, it could be checked that NIR and gamma ray, the gamma ray image and the NIR image not only matched well, but detection sensitivities thereof were also high enough that the gamma ray compensated the NIR image.

Figure 13:
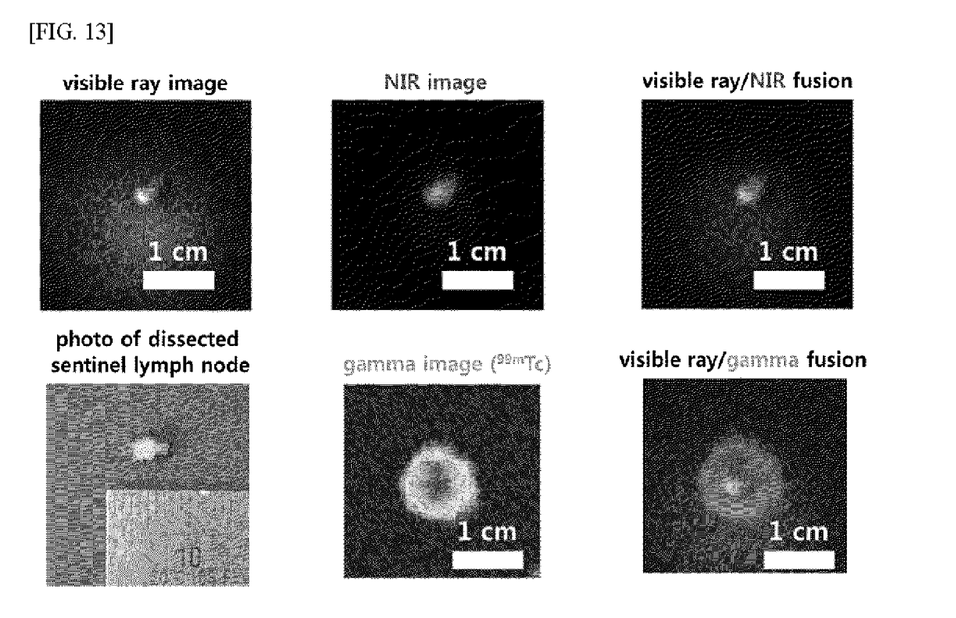
FIG. 13 shows sequential images and a superimposition image of visible ray/near infrared light/gamma ray images obtained by imaging, with a triple fusion imaging device according to an embodiment of the present invention, a sentinel lymph node dissected from a mouse to which a mixture of a gamma ray emission radioactive material ($^{99m}$Gc-Sb colloid) and a near infrared ray fluorescence material (ICG) is injected.

FIG. 13 shows sequential images and a superimposition image of visible ray/near infrared light/gamma ray images obtained by imaging, with a triple fusion imaging device according to an embodiment of the present invention, a sentinel lymph node dissected from a mouse to which a mixture of a gamma ray emission radioactive material ($^{99m}$Tc-antimony sulfide colloid) and an NIR fluorescence material (ICG) is injected. As shown, it was checked, through the visible ray, NIR and gamma ray images, that $^{99m}$Tc+ICG is effectively integrated to the dissected sentinel lymph node.

Consequently, a triple fusion imaging device according to an embodiment of the present invention enables fusion of visible ray, NIR, and gamma ray images to be accurately and rapidly processed by equalizing visual fields of a visible ray, an NIR, and a gamma ray, and provides a visible ray/NIR/gamma ray fusion image within several tens of seconds, e.g. 30 seconds, to enable a surgery doctor to effectively remove a sentinel lymph node while watching the fusion image.

While the present invention has been described in connection with the exemplary embodiments illustrated in the drawings, it is to be understood that various equivalent modifications and variations of the embodiments can be made by a person having an ordinary skill in the art without departing from the spirit and scope of the present invention.

DESCRIPTION OF REFERENCE NUMERALS 100, 200: Triple fusion imaging device
110, 210: Composite laparoscope for near infrared ray/gamma ray/visible ray image acquisition
111, 211: Optical source
112, 212: Focusing lens
114, 214: Pinhole collimator
116, 216: GSO scintillation crystal
118, 218: Fiber optic taper
120, 220: Optical fiber
130, 230: Optical-to-electrical conversion module
131, 134: Dichroic mirror
132, 135, 137: Bandpass filter
232: Filter rotator
133, 136, 138, 236: CCD
140, 240: PC

The invention claimed is:

1. A triple fusion imaging device for sentinel lymphadenectomy for laparoscopic surgery comprising:
a composite laparoscope for near infrared rat/gamma ray/visible ray acquisition configured to acquire triple images of a gamma ray from a gamma ray emitting radioactive material injected to a diseased part, a visible ray, and a near infrared ray;
an optical fiber configured to transmit the triple images acquired from the composite laparoscope;
wherein the composite laparoscope for near infrared ray/gamma ray/visible ray acquisition configured to acquire triple images configured from:
a lens configured to focus the visible ray and the near infrared ray to a focal plane,
a collimator configured to remove an unnecessary background gamma ray for gamma ray imaging or counting scheme, and for acquiring a wide field of view image,
a gamma ray scintillation crystal configured to obtain a gamma ray scintillation image by an interaction with a gamma ray emitted from a radioactive material injected to the diseased part, and
an optical mechanism by which the sensitivities and resolutions of the near infrared ray and gamma ray are adjustable by changing the distances between at least two parts among the lens, the collimator and the gamma ray scintillation crystal;
an optical fiber configured to transmit the triple images acquired from the composite laparoscope;
an optical source configured to generate a white light for acquiring a visible image through the optical fiber and a near infrared ray excitation light for acquiring a near infrared ray image by exciting a near infrared ray emitting fluorescence material at the disease part;
an optical-to-electrical conversion module configured to separate individual images of the visible ray, near infrared ray and gamma ray from the triple images delivered through the optical fiber and then respectively convert the individual images to electrical signals;
a matching unit configured to match a visible image signal, a near infrared image signal and a gamma ray image signal from the optical-to-electrical conversion module to one image; and
an image display unit configured to display the image from the matching unit.

2. The triple fusion imaging device for sentinel lymphadenectomy for laparoscopic surgery according to claim 1, wherein the collimator is a diverging collimator, a parallel-hole collimator, or a single or multi- pinhole collimator.

3. The triple fusion imaging device for sentinel lymphadenectomy for laparoscopic surgery according to claim 2, wherein, when the collimator is a pinhole collimator and a diameter of the pinhole is D, a unique resolution of the gamma ray, point source sensitivities and sheet source sensitivities of the gamma ray, the near infrared ray and the visible ray are determined by prescribed equations.

4. The triple fusion imaging device for sentinel lymphadenectomy for laparoscopic surgery according to claim 3, wherein, in the pinhole collimator, a tungsten collimator is replaceable by another by using a rotary wheel, and 5 to 7 tungsten blades of which are assembled to freely adjust a diameter of a hole from 0.5 mm to 8 mm.

5. The triple fusion imaging device for sentinel lymphadenectomy for laparoscopic surgery according to claim 1, wherein the near infrared ray emitting fluorescence material is indocyanine green.

6. The triple fusion imaging device for sentinel lymphadenectomy for laparoscopic surgery according to claim 1, wherein the gamma ray radioactive material is a compound containing $^{99m}$Tc.

7. The triple fusion imaging device for sentinel lymphadenectomy for laparoscopic surgery according to claim 6, wherein the compound containing $^{99m}$Tc is $^{99m}$Tc-antimony sulfide, $^{99m}$Tc-sulfur colloid, $^{99m}$Tc-nanocolloid, $^{99m}$Tc-human serum albumin, or $^{99m}$Tc-phytate colloid.

8. The triple fusion imaging device for sentinel lymphadenectomy for laparoscopic surgery according to claim 1, wherein the gamma ray scintillation crystal is GSO, BGO, or CsI(Tl).

9. The triple fusion imaging device for sentinel lymphadenectomy for laparoscopic surgery according to claim 1, wherein the optical-to electrical conversion module is configured from:
a first dichroic mirror configured to separate a gamma ray scintillation in a 400 to 500 nm band from a light incident through the optical fiber;
a first bandpass filter configured to pass only the gamma ray scintillation in the 400 to 500 nm band;
a first CCD configured to convert the gamma ray scintillation in the 400 to 500 nm band to an electrical signal;
a second dichroic mirror configured to separate a visible ray in a 500 to 700 nm band from a light passing through the first dichroic mirror;
a second bandpass filter configured to pass only the visible ray in the 500 to 700 nm band;
a second CCD configured to convert the visible ray in the 500 to 700 nm band to an electrical signal; and
a third bandpass filter configured to pass only a near infrared ray in a 790 to 875 nm band from a light passing through the second dichroic mirror; and
a third CCD configured to convert the near infrared ray in the 790 to 875 nm band to an electrical signal.

10. The triple fusion imaging device for sentinel lymphadenectomy for laparoscopic surgery according to claim 1, wherein the optical-to-electrical conversion module is configured from:
one CCD; and
a filter rotator configured from:
a first bandpass filter configured to pass only a gamma ray scintillation in a 400 to 500 nm band;
a second bandpass filter configured to only pass a visible ray in a 500 to 700 nm band; and
a third bandpass filter configured to pass only an infrared ray in a 790 to 875 nm band.

11. The triple fusion imaging device for sentinel lymphadenectomy for laparoscopic surgery according to claim 1, wherein the matching unit, by being implemented with a computer (PC) configured to remove a noise so as to make each CCD image input from the optical-to-electrical conversion module have the same visual field, removes a noise for each frame of a gamma ray signal image incident to a first CCD with a median filter, and a total brightness value and a number of pixels having a value equal to or greater than a threshold value calculated in advance are calculated to be available as a real time counting mode.

12. The triple fusion imaging device for sentinel lymphadenectomy for laparoscopic surgery according to claim 1, further comprising:
   a fiber optic taper configured to deliver the visible ray image, near infrared ray image, and the gamma ray image to the optical fiber.

* * * * *